United States Patent [19]

Armor

[11] 4,163,756

[45] Aug. 7, 1979

[54] DIRECT OXIMATION OF KETONES

[75] Inventor: John N. Armor, Morris Plains, N.J.

[73] Assignee: Allied Chemical Corporation, Morris Township, Morris County, N.J.

[21] Appl. No.: 895,325

[22] Filed: Apr. 11, 1978

[51] Int. Cl.$^2$ .................. C07C 131/04; C07C 131/00
[52] U.S. Cl. ................................................. 260/566 A
[58] Field of Search ..................................... 260/566 A

[56] References Cited

U.S. PATENT DOCUMENTS 3,503,958   3/1970   Landis ............................... 260/239.3

OTHER PUBLICATIONS

Knauss, Z. Phys. Chem., Part B., vol. 39, No. 2, pp. 83–100, (1938).
Kirk-Othner, Encyclopedia of Chem. Technology, vol. 11, pp. 494–495, (1966).
Knauss et al., Z. Phys. Chem., Part B., vol. 45, No. 1, pp. 1–18, (1939).
Chem. Abstr., vol. 34, col. 931(8), (1940).
Chem. Abstr., vol. 32, col. 4865(4), (1938).
Chem. Abstr., vol. 45, col. 29(g), (1951).
Chem. Abstr., vol. 41, col. 1945(b), (1947).

*Primary Examiner*—Gerald A. Schwartz
*Attorney, Agent, or Firm*—Robert A. Harman

[57] ABSTRACT

Ammonia, oxygen e.g., as air, and a ketone react in contact with a catalyst such as porous, amorphous silica or alumina which may or may not have a coating to form an oxime, at temperatures such as 50°–500° C. The oximes have known utilities, including uses as oxidation inhibitors and as intermediates for production of amides. In particular, when the ketone is cyclohexanone, the cyclohexanone oxime in the reaction product can further be converted to the cyclic amide, caprolactam, e.g. by contacting the product with an aluminosilicate catalyst having average pore diameter of at least 7 angstroms, especially a molecular sieve, suitably downstream in the same reaction vessel. Caprolactam is the monomer starting material for nylon 6.

8 Claims, No Drawings

DIRECT OXIMATION OF KETONES

BACKGROUND OF THE INVENTION

This application relates to oxidation of ammonia whereby direct oximation of ketones is achieved.

It is known that ammonia can be oxidized at high temperatures such as 780° C. by air producing mainly nitrogen and water together with small traces of ammonium nitrate and nitrogen dioxide. By use of a catalyst such as platinum gauze, or Pt/Rh, it is known to oxidize ammonia with air to nitric oxide. The nitric oxide reacts further with oxygen of air to form nirogen dioxide which is absorbed in water to form nitric acid. The normal commercial process for production of the partial ozidation product, hydroxylamine, is by oxidation of ammonia to nitrogen oxides over cobalt oxide catalyst, followed by reduction of nitrogen oxides using sulfur dioxide in the so called Raschig process, or by reduction of nitric oxide by hydrogen over a platinum on carbon catalyst. It has also been reported that ammonia is oxidized by oxygen to hydroxylamine plus nitrous acid as the main products condensed on the vessel walls (by liquid air cooling), when passed over a platinum catalyst at low pressure and at very high temperatures (740°-1350° C.)—W. Kraus, Z. Phys. Chem. Part B, vol. 39 of 1938, pg. 83; vol. 45 of 1939, pg. 1; Z Elektrochem. vol. 54 of 1950, pg. 264; also that ammonia adsorbed on activated carbon in presence of air and water vapor forms hydroxylamine (C. Courtny et al., Comptes Rendus vol. 223 of 1946, page 624). See Chemical Abstracts vol. 34 of 1940 col. 931(8); vol. 32 of 1938, col. 4865(4); vol. 45 of 1951 col. 29(g); vol. 41 of 1947 col. 1945(b).

SUMMARY OF THE INVENTION

In the present process, ammonia and oxygen such as oxygen of the air are mixed with a ketone and contacted with a solid catalyst, especially a catalyst comprising silica and/or alumina and/or boron nitride, and/or magnesia, and/or zirconia, and/or zinc oxide, and/or an oxide of a transition metal of Group 3-8 of the Periodic Table, said catalyst having surface area of at least 1 but not over 900 square meters per gram.

At suitable temperatures in the broad range of 50°-500° C., the oxime of said ketone is thereby formed in a form which can be recovered as a reaction product.

DETAILED DESCRIPTION AND PREFERRED EMBODIMENTS

In a preferred embodiment of the invention, the ketone employed is cyclohexanone, the resulting oxime being cyclohexanone oxime. It is known (U.S. Pat. No. 3,503,958 of Mar. 31, 1970 to P. S. Landis) that oximes containing 3-20 carbon atoms can be rearranged in liquid or vapor phase, using certain conditions, over aluminosilicate catalyst such as the zeolites and the molecular sieve materials to produce valuable industrial products such as caprolactam from cyclohexanone oxime. The catalyst should have average pore diameter of at least 7 angstroms. Accordingly, the reaction product of the present process can be passed into contact with an aluminosilicate catalyst having average port diameter of at least 7 angstroms, more particularly at least 10 angstroms, at temperatures such as about 170°-370° C. Thereby at least a partial conversion of the oxime in the product to an amide is obtained. If desired, this conversion can be downstream in the same reaction vessel as used for the ammonia/ketone/oxygen reaction, using a sufficiently large bed of rearrangement catalyst to obtain optimum conversion of the oxime to amide. The amide can be recovered and the unreacted ketone and oxime can be recycled.

In the present process, the reactants can be introduced into the reaction zone and the oxime product can be removed therefrom in the gaseous state, or the ketone can be in the liquid state, e.g., in solution, with ammonia and oxygen also in solution and/or dispersed in the liquid. The reaction can be conducted in the liquid phase, or in a trickle mode; preferably it is conducted entirely in the vapor phase.

For operation in the vapor phase, suitably but not necessarily, the present process is operated using excess ammonia, and about equivalent ketone:oxygen proportions. For safety reasons it is desirable to maintain the proportions of reactants outside the explosive limits (which for ammonia in air are about 15%-28% by volume); and for ketone in air are about 1%-8% by volume). A series of inlets for one or more of the reactants can be used to control the proportions of reactants present.

Diluent gas can be used to keep the composition out of the explosive range and/or to assist removal of oxime adsorbed on the catalyst. A liquid solvent can be used for removal of oxime from the catalyst, either intermittently or continuously trickling over the catalyst or flushing out organic material from the catalyst.

The reaction time allowed in passing the reaction mixture vapors through the bed of solid catalyst of oxime production is generally from about 0.1 to 10 seconds of contact time. The total pressure will generally be in the range from about 1 to 50 atmospheres, especially 1 to 10 atmospheres. The preferred temperature range for reaction of cycloalkyl, dialkyl and alkyl aryl ketones is about 60°-400° C.; and more specifically for cyclohexanone is about 120°-250° C.

The most effective catalysts appear to be porous, amorphous silicas and aluminas, especially porous, amorphous silica having surface area in the range of 100-500 sq. m./gram. Specific catalysts found to be operative, in addition to such silicas and aluminas, include the fumed (i.e. pyrogenic) form of silica; the natural and artificial zeolites (i.e. porous crystalline aluminosilicates) impregnated with one or another known oxidation promoters such as transition metals or oxides including Co, Mo, La, Rh, Pt; also other solid catalysts including magnesia, titania, zirconia, zinc oxide, and bismuth oxide or cobalt oxide mixed with molybdenum oxide, each alone and supported on porous silica or alumina; also titania/silica; porous crystalline aluminosilicates such as montmorillonite; boron nitride.

Ketones which can be used must, of course, be reasonably stable at the reaction conditions of temperature, time and catalyst. In general any cycloalkyl, dialkyl, or alkyl aryl ketone having 3-20 carbon atoms can be used, such as acetone, methylethyl ketone, methyl isopropyl ketone, ethyl butyl ketone, the pentanones, cyclohexanone, methylcyclohexanone, norcamphor, cyclopentanone, cyclohexyl methyl ketone, acetophenone, and methyl benzyl ketone. Alcohols oxidizable to ketones, e.g. cyclohexanol, can also be used as starting materials in my process.

The examples which follow are illustrative of this invention and of the best mode contemplated by me for carrying out the invention, but are not to be interpreted in a limiting sense.

In these Examples, the reaction was carried out in a borosilicate glass tube of about 14 mm. outside diameter, containing a glass frit or a plug of quartz wool to hold the catalyst in place. The glass tube reactor, equipped for downward feed of the reactants in the gas phase in cocurrent flow, was contained inside a tube furnace, electrically heated. As the bed was made deeper, under otherwise the same conditions, the extent of conversion increased. The depth of catalyst bed was varied; typically it was about 1–2.5 cm. The temperature, measured at the wall of the furnace, was maintained practically constant at the values stated in the Examples. The reactor was operated manually and also automatically using a cam timer to actuate the sampling valves for reactants and products.

The ketone was fed as vapor from a saturator or as liquid by a pump and vaporized at the top of the reactor in a bed of quartz chips. The products emerging from the bottom of the reactor passed through heated lines into an ice cooled trap containing methanol or ethanol. Samples were diverted continuously for analysis by gas chromatography.

EXAMPLE 1

0.8 gms of Porasil A, 80–100 mesh, available from Waters Associates, Framingham, Mass., was added to the reactor tube as catalyst. This material consists essentially of porous, amorphous silica gel spherical beads, described by the manufacturer as having average pore diameter of 100 angstroms and surface area per gram of 350–500 sq. m. Cyclohexanone was vaporized in a saturator at a rate of about 0.65 cc (as vapor) per minute into a gas stream of nitrogen (3.7 cc/min.) to which ammonia gas (12.0 cc/min.) and oxygen gas (1.0 cc/min.) were added. The furnace temperature was maintained at 194° C.

There was a lag in the production of cyclohexanone oxime, after which a selectivity (to oxime) of 51%, at 54% conversion of the ketone was obtained (i.e. a yield of oxime of 28% of theory based on the cyclohexanone employed).

EXAMPLE 2

With about 2.0 gms of the above described Porasil A as catalyst in a reactor of the type above described, cyclohexanone was fed at about 0.7 cc/min (as the vapor) along with $NH_3$ (15 cc/min.), $O_2$ at 1 cc/min, and $N_2$ at 8.7 cc/min. At a temperature of 194° C. the selectivity to oxime was 42%, at 93% conversion of the ketone (yield of oxime=39%).

EXAMPLE 3

Using 2.7 gm of commercial gamma-alumina (20–40 mesh) contained in the above described reactor, 0.004 cc cyclohexanone (as the liquid) per minute was fed along with $NH_3$ (18 cc/min) and air (40 cc/min.). At 183° C., the selectivity to cyclohexanone oxime was 23% with 83% conversion of the ketone (yield of oxime=19%). The gamma-alumina had a wide distribution of pore diameters and surface area of about 220 sq. m. per gram.

EXAMPLE 4

Using 1.0 gm of the above described Porasil A (80–100 mesh) contained in a reactor as above described, acetone vapor (1.2 cc/min.) was passed through the catalyst bed along with $NH_3$ (16 cc/min.), air (4 cc/min.) and additional $N_2$ at 2 cc/min. At a temperature of 250° C., a selectivity to acetone oxime of 22% with 90% conversion of the acetone was achieved, i.e. a yield of 20% of theory.

Other ketones tested similarly and found to produce the corresponding oximes were 3-pentanone (tested at 230° C.) and acetophenone (tested at 280° C.).

EXAMPLE 5

In apparatus as in the foregoing Examples, a 2.5 cm. deep bed of gamma-alumina catalyst of Example 3 was succeeded downstream by a 5 cm. deep bed of lanthanum-coated molecular sieve. Cyclohexanone (0.01 cc per minute as liquid) was fed into the reactor together with 25 cc of ammonia gas per minute and 40 cc of air per minute. The reaction temperature was 250° C.

Analysis of the products showed a yield of cyclohexanone oxime of about 10% of theory (based on the cyclohexanone employed) plus caprolactam in yield of about 4% of theory.

EXAMPLE 6

Using more elevated temperature and lower oxygen concentration, oxime was obtained over the catalyst of Example 1. Thus at 228° C., 10 cc/min. of ammonia, 2 cc/min. of air, and 15 cc/min. of nitrogen (cyclohexanone 0.65 cc/min. vapor) the selectivity to oxime was 22% and conversion of cyclohexanone was 92% (i.e. 20% yield of oxime).

EXAMPLE 7

Using apparatus and procedure as in the foregoing Examples, a series of porous, amorphous silica beads having narrow ranges of pore diameters, available from Corning Glass Works as Controlled Pore Glasses, was employed as catalysts with cyclohexanone, with the following results:

| Catalyst | Surf.Area (sq.m./gm.) | Avg. Pore Diam. | Selectivity to Oxime |
|---|---|---|---|
| CPG - 75 | 240 | 75 angstroms | Ca. 50% |
| CPG - 175 | Ca. 100 | 175 angstroms | 23% |
| CPG - 2000 | Ca. 9 | 2000 angstroms | 5% |

In these tests the feed was cyclohexanone, 0.0025 cc/min. of liquid (which was then vaporized); $NH_3$ gas, 12 cc/min; air, 4 cc/min. The temperature was 185° C. and the volume occupied by the catalyst was 2 cc. These catalysts are described by the manufacturer as being prepared from borosilicate glass, heated to cause separation of the ingredients and then etched to remove borates.

I claim:

1. Direct process for production of oxime which comprises passing a mixture consisting essentially of a ketone, ammonia and oxygen in contact with a solid catalyst said catalyst having surface area of at least one and up to 900 square meters per gram, at temperature in the range of 50° C.–500° C., thereby producing oxime in recoverable form as a reaction product wherein the solid catalyst comprises silica, alumina, boron nitride, magnesia, zirconia, zinc oxide, or an oxide of a transition metal of Group 3-8 of the Periodic Table or mixtures thereof.

2. Process of claim 1 wherein the temperature is in the range from about 60° C. up to about 400° C. and wherein the catalyst comprises a porous, amorphous silica or a porous, amorphous alumina.

3. Process of claim 2 wherein a liquid solvent for the oxime product is employed to assist the removal of oxime from catalyst.

4. Process of claim 2 wherein the reaction is conducted in the vapor phase employing diluent gas.

5. Process of claim 2 wherein the ketone is a cycloalkyl, dialkyl, or alkyl aryl ketone having 3–20 carbon atoms.

6. Process of claim 5 wherein the ketone is cyclohexanone.

7. Process of claim 6 wherein the catalyst consists essentially of silica and the catalyst has surface area in the range of 100–500 sq. m. per gram.

8. Process of claim 7 wherein the temperature is in the range 120° C.–250° C. and the reaction is conducted in the vapor phase employing diluent gas.

* * * * *